(12) United States Patent
Hultine et al.

(10) Patent No.: US 11,180,371 B2
(45) Date of Patent: Nov. 23, 2021

(54) INTEGRATED SYNTHESIS OF COMMODITY CHEMICALS FROM WASTE PLASTIC

(71) Applicants: J. Dustin Hultine, Milwaukie, OR (US); Robert Kurt Graupner, Hillsboro, OR (US)

(72) Inventors: J. Dustin Hultine, Milwaukie, OR (US); Robert Kurt Graupner, Hillsboro, OR (US)

( * ) Notice: Subject to any disclaimer, the term of this patent is extended or adjusted under 35 U.S.C. 154(b) by 19 days.

(21) Appl. No.: 16/834,720

(22) Filed: Mar. 30, 2020

(65) Prior Publication Data

US 2020/0325021 A1 Oct. 15, 2020

Related U.S. Application Data (60) Provisional application No. 62/920,133, filed on Apr. 12, 2019, provisional application No. 62/922,000, filed on Jul. 17, 2019.

(51) Int. Cl.
| | | |
|---|---|---|
| *C01B 32/05* | (2017.01) | |
| *C07C 277/02* | (2006.01) | |
| *C01B 3/12* | (2006.01) | |
| *C07D 251/58* | (2006.01) | |

(52) U.S. Cl.
CPC ............ *C01B 32/05* (2017.08); *C01B 3/12* (2013.01); *C07C 277/02* (2013.01); *C07D 251/58* (2013.01); *C01B 2203/0283* (2013.01)

(58) Field of Classification Search
CPC ..... C07C 277/02; C07C 227/00; C01B 32/05; C01B 3/12; C01B 2203/0283; C07D 251/58; C01C 3/002
See application file for complete search history.

(56) References Cited

U.S. PATENT DOCUMENTS

| 2,917,371 A | 12/1959 | Fischer et al. |
| 2,952,591 A | 9/1960 | Finn, Jr. et al. |
| 3,300,281 A | 1/1967 | May |
| 3,403,053 A | 9/1968 | Del Duca |

(Continued)

FOREIGN PATENT DOCUMENTS

| CN | 1493537 A | 5/2004 |
| CN | 101186316 A | 5/2008 |

(Continued)

OTHER PUBLICATIONS

Meyer F., "Producing carbide using plastic waste," BINE Information Service, 2011, 4 pages.

(Continued)

*Primary Examiner* — Jafar F Parsa
(74) *Attorney, Agent, or Firm* — Alleman Hall Creasman & Tuttle LLP (57) ABSTRACT

A process to extract carbon from hydrophobic waste comprises: combining the hydrophobic waste with an oxide of an active metal to form a storable, moisture-resistant feedstock for high-temperature processing; heating the feedstock in a furnace to yield an effluent gas entraining a carbide of the active metal; cooling the effluent gas entraining the carbide of the active metal; introducing nitrogen into the cooled effluent gas entraining the carbide of the active metal, to yield a cyanamide of the active metal and elemental carbon; and acidically hydrolyzing the cyanamide of the active metal to yield a cyanamide compound and a salt of the active metal.

20 Claims, 5 Drawing Sheets

(56) References Cited

U.S. PATENT DOCUMENTS

| | | | |
|---|---|---|---|
| 4,013,757 | A | 3/1977 | Berkowitz et al. |
| 4,220,635 | A | 9/1980 | Schell |
| 4,477,421 | A | 10/1984 | Weiss |
| 5,753,199 | A | 5/1998 | Weber et al. |
| 7,060,233 | B1 | 6/2006 | Srinivas et al. |
| 7,140,187 | B2 | 11/2006 | Amendola |
| 7,912,358 | B2 | 3/2011 | Stone, Jr. et al. |
| 2007/0266623 | A1 | 11/2007 | Paoluccio |
| 2008/0286165 | A1 | 11/2008 | Graupner et al. |
| 2015/0238922 | A1 | 8/2015 | Kambara et al. |

FOREIGN PATENT DOCUMENTS

| | | |
|---|---|---|
| CN | 100537421 C | 9/2009 |
| CN | 102268686 A | 12/2011 |
| CN | 102701215 A | 10/2012 |
| CN | 102936211 A | 2/2013 |
| CN | 103408392 A | 11/2013 |
| DE | 4339403 A1 | 5/1995 |
| DE | 102008031293 A1 | 1/2010 |
| FR | 2797891 A1 | 3/2001 |
| GB | 245719 A | 10/1926 |
| GB | 275145 A | 2/1928 |
| GB | 393128 A | 6/1933 |
| GB | 465421 A | 5/1937 |
| GB | 701162 A | 12/1953 |
| GB | 720170 A | 12/1954 |
| GB | 771310 A | 3/1957 |
| GB | 935503 A | 8/1963 |
| GB | 1173109 A | 12/1969 |
| GB | 1326933 A | 7/1975 |
| JP | 2003040602 A | 2/2003 |
| JP | 2005145748 A | 6/2005 |
| JP | 2012071291 A | 4/2012 |
| WO | 9106509 A | 5/1991 |
| WO | 2005108289 A3 | 11/2005 |
| WO | 2012123378 A1 | 9/2012 |
| WO | 2012123380 A3 | 9/2012 |

OTHER PUBLICATIONS

Buettner, L et al., "Instantaneous Ignition of Activated Carbon," Industrial & Engineering Chemistry Research, Sep. 19, 2014, 5 pages.

Venable, F et al., "Some of the Properties of Calcium Carbide," Journal of the Elisha Mitchell Scientific Society, vol. 12, No. 1, 1895, 8 pages.

"Cement Emissions," Cement Industry Federation, Available Online at http://www.cement.org.au/SustainabilityNew/ClimateChange/CementEmissions.aspx, Retrieved on Mar. 26, 2020, 1 page.

Diaz, A et al., "Magnesium Carbide Synthesis From Methane and Magnesium Oxide—A Potential Methodology for Natural Gas Conversion to Premium Fuels and Chemicals," Proceedings of the U.S. DOE Coal Liquefaction and Gas Conversion Contractor's Review Conference (Gas-to-Liquids Session), Pittsburgh, Pennsylvania, Aug. 29, 1995.

Pranke, E., "Cyanamid Manufacture, Chemistry and Uses," The Chemical Publishing Company, Easton, PA, 1913, 132 pages.

Pourcelly, G., "Electrodialysis with Bipolar Membranes: Principles, Optimization, and Applications," Russian Journal of Electrochemistry, Aug. 2002, 9 pages.

Behzad, H. et al., "Ultrafine coal dewatering: Relationship between hydrophilic lipophilic balance (HLB) of surfactants and coal rank," International Journal of Mineral Processing, Oct. 25, 2014, 8 pages.

"Hydrogen cyanide Immediately Dangerous to Life or Health Concentrations (IDLH)," Available online at https://www.cdc.gov/niosh/idlh/74908.html, May 1994.

Kim, C et al., "CaC2 Production from CaO and Coal or Hydrocarbons in a Rotating-Arc Reactor," Industrial & Engineering Chemistry Process Design and Development, Apr. 1979, 6 pages.

H., G. "Metallic Carbides," Nature, No. 398, vol. 54, Aug. 13, 1896 1 page.

Osterberg, A., "The Preparation of Cyanamide," Chemical Laboratory of the Mayo Clinic, Oct. 11, 1917, 3 pages.

Fincke, J et al., "Thermal Conversion of Methane to Acetylene Final Report," Idaho National Engineering and Environmental Laboratory, Jan. 2000, 69 pages.

International Search Report and Written Opinion Issued in Application No. PCT/US2020/027098, dated Jun. 12, 2020, WIPO, 9 pages.

"CSB Releases Draft Final Report on Carbide Industries Explosion that Killed Two in Louisville, Kentucky in 2011; Company Ignored Years of Smaller, Similar Incidents in Electric Arc Furnace," U.S. Chemical Safety Board, Available Online at https://www.csb.gov/csb-releases-draft-final-report-on-carbide-industries-explosion-that-killed-two-in-louisville-kentucky-in-2011-company-ignored-years-of-smaller-similar-incidents-in-electric-arc-furnace-/, Feb. 7, 2013, 4 pages.

"Methanol Price and Supply/Demand," Methanol Institute, Available Online at https://www.methanol.org/methanol-price-supply-demand/, Available as Early as Apr. 29, 2019, 4 pages.

Xiong, W. et al., "Heterogeneous Phases Reaction Equilibrium in an Oxy-Thermal Carbide Furnace," ChemEngineering, vol. 4, No. 2, Jan. 3, 2020, 18 pages.

INTEGRATED SYNTHESIS OF COMMODITY CHEMICALS FROM WASTE PLASTIC

CROSS-REFERENCE TO RELATED APPLICATIONS

This application claims priority to U.S. Provisional Patent Application Ser. No. 62/920,133, filed Apr. 12, 2019, and entitled METHODS FOR CONTINUOUS PRODUCTION OF CYANAMIDE-RELATED COMPOUNDS FROM ENCAPSULATED CALCIUM OXIDE; and to U.S. Provisional Patent Application Ser. No. 62/922,000, filed Jul. 17, 2019, and entitled CONTINUOUS PRODUCTION OF CYANOGUANIDINE WITHOUT CARBON DIOXIDE EMISSION, the entirety of all of which are hereby incorporated herein by reference for all purposes.

TECHNICAL FIELD

The disclosure herein relates generally to the field of chemical engineering and more specifically to environmentally sustainable conversion of waste plastic into high-value commodity chemicals.

BRIEF DESCRIPTION OF THE DRAWINGS

The disclosure herein will be better understood from reading the following Detailed Description with reference to the attached drawing figures, wherein.

DETAILED DESCRIPTION

Waste plastic is discharged into the environment at an alarming rate. This material occupies valuable space in landfills, biodegrades very slowly, and has a tendency to escape intended waste-disposal routes and proliferate on land and sea. Increasing evidence points to an overall negative impact of proliferated waste plastic on the global environment.

An attractive path to reducing the discharge of waste plastic is through plastic recycling. However, many different types of plastic enter the waste stream, and, generally speaking, each type must be recycled separately. Accordingly, an extensive sorting and recycling infrastructure is required in order to handle even the most prolific types of plastic. Furthermore, in contrast to the recycling of metals, there is little economic incentive driving the recycling of plastics, which are relatively inexpensive to manufacture from virgin material.

Nevertheless, waste plastic is a potentially valuable source of reduced carbon. Accordingly, one alternative to plastic recycling is to subject waste plastic to reforming conditions to yield products such as carbon monoxide (CO) and hydrogen ($H_2$), which may be converted into valuable commodity chemicals or used as fuel. However, reformer technologies typically employ heterogeneous catalysts that may be poisoned by heteroatoms in the feedstock. Such heteroatoms may include halogens such as chlorine (Cl) and fluorine (F), which are ubiquitous in waste-plastic streams. Even in scenarios in which the catalyst resists poisoning, the reforming of halogenated compounds and subsequent use of the reformate may result in the discharge of undesirable halogenated gasses into the environment.

In view of the foregoing issues, an alternative process for extracting the reduced-carbon content of waste plastic and converting it into valuable commodity chemicals is disclosed herein. The integrated process transforms waste plastic into 2-cyanoguanidine (2-CG) and/or related compounds through a series of intermediates that include active metal carbides and cyanamides. In one implementation, the process uses ordinary lime (calcium oxide, CaO) as a mostly recoverable source of the active metal. The process does not require a catalyst susceptible to poisoning by heteroatoms but sequesters the halogen content of the waste plastic in the form of stable and innocuous inorganic salts. The process includes various material- and energy-recovery features that improve thermal efficiency, reduce material utilization, and provide other sustainability advantages.

The compact description above is intended to introduce a portion of this disclosure in simplified form, not to identify key or essential features. Set forth in the appended claims, the subject matter claimed herein is limited neither to the content above nor to implementations that address any problems or disadvantages noted in any part of this disclosure.

Additional features will now be presented by way of example and with reference to the drawing figures listed further above. Components, process steps, and other elements that may be substantially the same in one or more of the figures are identified coordinately and are described with minimal repetition. It will be noted, however, that elements identified coordinately may also differ to some degree. It will be further noted that the figures are schematic and generally not drawn to scale. Rather, the various drawing scales, aspect ratios, and numbers of components shown in the figures may be purposely distorted to make certain features or relationships easier to see.

Figure 1:
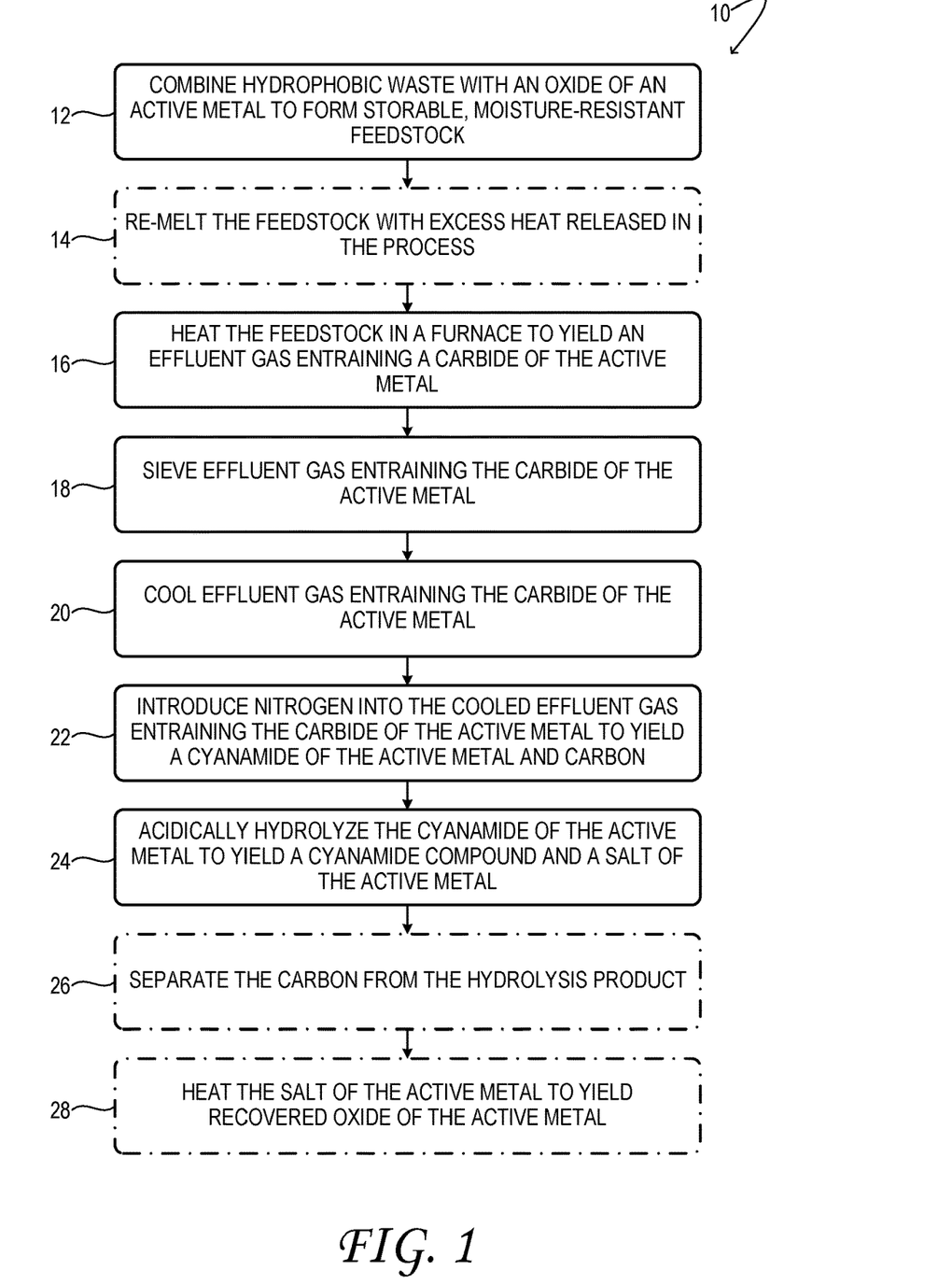
FIG. 1 shows aspects of an example process to extract carbon from hydrophobic waste.

FIG. 1 shows aspects of an example process 10 to extract carbon from hydrophobic waste. In contrast to an incineration process, which would release the carbon content of the waste as carbon dioxide ($CO_2$), process 10 extracts the carbon content in a useful, reduced form. More particularly, process 10 extracts the carbon in the form of 2-cyanoganidine and/or related commodity chemicals. The term 'reduced', as applied to the element carbon, will be understood in the context of reduction-oxidation (redox) chemistry. The term 'hydrophobic waste' will be understood to include any waste material that is substantially water-repellant, water-insoluble and/or non-water-absorbing. Non-limiting examples of hydrophobic waste include waste plastic, roof shingle, and motor-vehicle tires.

At 12 of process 10, hydrophobic waste is combined with an oxide of an active metal to form a storable, moisture-resistant feedstock for high-temperature processing. As used herein, the term 'active metal' refers generically to metallic elements of groups IA and IIA of the Periodic Table of the Elements. In more particular examples, this term is restricted to relatively abundant and toxicologically and environmentally benign elements from groups IA and IIA—such as sodium, potassium, magnesium, and calcium. In some examples, accordingly, the oxide of the active metal includes CaO. In some examples, the oxide of the active metal includes sodium oxide ($Na_2O$). In some examples, the oxide of the active metal may include a mixture of oxides of different active metals.

As noted above, the hydrophobic waste in some examples may include waste plastic. Non-limiting examples of waste plastic include polypropylene (PP), polyethylene (PE), polystyrene, polyethylene terephthalate (PET), nylon, polyvinylchloride (PVC), acrylonitrile butadiene styrene (ABS), poly (methyl methacrylate) (PMMA), polycarbonate (PC), and polytetrafluoroethylene (PTFE). More generally, waste plastic may include any commonly used thermoplastic polymer or copolymer material or mixture thereof. In some examples, the thermoplastic polymer or copolymer material may be combined with thermosetting and/or cross-linked polymer materials and/or non-polymeric plasticizers. Alternatively or in addition, the hydrophobic waste may include non-plastic components, such as roof shingle and/or motor-vehicle tires.

The hydrophobic waste may be combined with the oxide of the active metal in any suitable manner. The hydrophobic waste may be conducted through a chipper and therein chipped to a desirable particle size distribution prior to combination with the oxide of the active metal, for instance. In other examples, the hydrophobic waste may be shredded or otherwise broken into fragments of suitable size. Active-metal oxide that is crushed, ground, and/or sieved to a suitable particle size may be combined with the fragmented hydrophobic waste at controlled proportions required for subsequent reaction of the feedstock.

In some examples, the hydrophobic waste may be heated to a melting or softening temperature before or during blending with the active metal oxide. The mixture of the hydrophobic waste and the active-metal oxide then may be extruded. In some examples, the extrusion process itself may release heat sufficient to soften the hydrophobic waste. By this or any other suitable encapsulation mechanism, the active-metal oxide is encapsulated in the hydrophobic waste, in the extruded material. Extrusions of feedstock comprising controlled proportions of blended hydrophobic waste and active-metal oxide may be cut or otherwise segmented to any desired length and stored until needed.

Storage of the active-metal oxide encapsulated in the hydrophobic waste admits of several advantages. First, encapsulation protects the active-metal oxide from ambient water vapor and carbon dioxide. Without benefit of the encapsulation, exposure of an active-metal oxide to atmospheric constituents is liable to degrade the material to the corresponding hydroxide—e.g., $$CaO + H_2O \rightarrow Ca(OH)_2, \tag{1}$$

and/or carbonate, $$CaO + CO_2 \rightarrow CaCO_3. \tag{2}$$

Second, encapsulation enables the active-metal oxide to be stored in a more environmentally responsible manner, as stored, encapsulated oxide material is less likely than non-encapsulated oxide material to be washed into a waterway in the event of excessive rainfall or flooding.

Third, the encapsulated material can be stored with the desired proportion of the active-metal oxide to the hydrophobic waste 'locked in' for subsequent reaction. This feature is valuable because process 10 may be engineered to consume various different active-metal oxides and various different forms of hydrophobic waste, even in the same production run. However, the optimal proportion of active-metal oxide to hydrophobic waste may vary depending on the forms being combined. Therefore, storage of the constituents already blended at the correct proportion and encapsulated alleviates the need for precise, variable metering of the constituents as they enter the feedstock-reactor system (vide infra).

In process 10, the carbon content of the hydrophobic waste is extracted and incorporated into a usable product. Accordingly, the feedstock need not include any source of carbon apart from the hydrophobic waste itself. In some examples, however, the overall conversion efficiency of process 10 may be improved by addition of elemental carbon to the feedstock. More particularly, the feedstock may include elemental carbon formed as a by-product of formation of the cyanamide intermediate and subsequently separated from the product, as described further below. The elemental carbon may be included in the blending and extrusion operations noted above. In examples in which elemental carbon is included in the feedstock, the proportion of waste plastic relative to active-metal oxide may be reduced to account for stoichiometric reaction of the elemental carbon with the active-metal oxide.

Subsequently in process 10, the feedstock is conveyed into a furnace for high-temperature processing. Generally speaking, the feedstock may be conveyed in any suitable form. The feedstock may be augured in solid form, for instance. Conveyance in softened solid, semisolid, and liquid forms is also envisaged. In some examples, the feedstock may be conveyed in the form of droplets or a continuous stream. At 14, accordingly, the feedstock is optionally re-melted with excess heat released in process 10, to facilitate conveyance into the furnace as a softened solid, semisolid, or liquid. The excess heat used to re-melt the feedstock may comprise heat recovered from cyanamide synthesis, from effluent-gas cooling, or from another point in the process (vide infra).

At 16 of process 10, the feedstock is heated in a furnace to yield an effluent gas entraining a carbide of the active metal. In a typical example, the feedstock is pre-heated in a chamber maintained at a relatively high pressure N. The feedstock may be heated to any temperature or range of temperatures suitable to pre-condition the feedstock for subsequent high-temperature heating. In one non-limiting example, the feedstock may be pre-heated to about 1300° C. The subsequent high-temperature heating may be enacted within an electric-arc furnace, although other furnace types are also envisaged. In some examples, an electric-arc furnace or other high-temperature heating stage may reach a temperature of about 2200° C. In examples in which the oxide of the active metal comprises calcium oxide, the reaction yields calcium carbide, $$CaO + 3C(\text{from hydrophobic waste}) \rightarrow CaC_2 + CO. \tag{3}$$

Other active-metal carbides, such as magnesium carbide, may be formed in the same manner.

Some waste plastics include chlorinated and/or fluorinated polymers. Without tying this disclosure to any particular theory, it is believed that the halogen component of the feedstock will associate with the active metal under the aggressive thermal conditions of eq 3, forming halide salts of the active metal—e.g., $CaCl_2$, $CaF_2$. This reaction pathway has been proposed in reported carbide synthesis using waste plastic in the feedstock.

In examples in which the feedstock is heated in an electric-arc furnace, the furnace may be ignited from an initial cold state by initiating an arc discharge through the gas within the furnace. Once the electric-arc furnace is in operation, gas released by the decomposition of the hydrophobic material and/or admitted as carrier gas (vide infra) will serve to sustain the arc. Such gas may include hydrogen, although various other arc-sustaining gasses are also envisaged. In some scenarios, accordingly, a portion of the effluent gas may be retained in the furnace to improve arc-heating efficiency.

In these and other examples, the feedstock may be heated under a flow of carrier gas admitted either to the furnace or fluidically upstream of the furnace. In examples in which a carrier gas is employed, the effluent gas that emerges from the furnace entraining the active-metal carbide includes the carrier gas. The carrier gas may be any gas that does not react with the active-metal oxide reactant or with the active-metal carbide intermediate at the operating temperatures of the furnace. In some examples, the carrier gas includes one or more of the inert gasses helium and argon. Alternatively or in addition, the carrier gas may include one or more of hydrogen and carbon dioxide, for instance.

In some examples, the rate of introduction of the carrier gas is controlled so as to influence the reaction kinetics of one or more stages of process 10. Such stages may include active-metal carbide formation at 16 and/or subsequent reaction of the active-metal carbide intermediate (vide infra). Generally speaking, increasing dilution with carrier gas reduces the rate of active-metal carbide formation because it cools the furnace. However, dilution may reduce the particle size distribution of the active-metal carbide intermediate, which increases the rate of the subsequent heterogeneous reaction of the intermediate.

At optional step 18, the effluent gas is subjected to a sieving operation, wherein the particles of the entrained active-metal carbide intermediate are size-selected upon discharge from the furnace. More particularly, only particles of sufficiently small size may be permitted to exit the furnace, thereby excluding highly agglomerated particles that may be less reactive toward cyanamide formation. In some examples, particles less than 100 microns, more preferably less than 20 microns, may be selected.

At 20 the effluent gas entraining the carbide of the active metal is cooled. More particularly, the effluent gas is cooled to a temperature suitable for subsequent transformation of the active-metal carbide into the corresponding active-metal cyanamide. In some examples, the effluent gas is cooled to about 1000° C. In some examples, cooling of the effluent gas may be effected by separating a portion of the flow of the effluent gas, actively or passively cooling that portion, and then re-introducing the cooled portion into the balance of the flow. The separated flow may be cooled by flowing through an air- or water-cooled chamber, for instance, or by flowing through an active heat exchanger.

Alternatively or in addition, the effluent gas entraining the active-metal carbide may be cooled via expansion. In particular, the effluent gas entraining the active-metal carbide may be discharged from the furnace into a chamber of pressure $P_2$, which is lower than N. Such cooling yields the carbide of the active metal in a controlled particle-size distribution. The reader will note that because the particle size distribution of the active-metal carbide is a function of the flow rate (vide supra), it is therefore also a function of the pressure differential $P_1 - P_2$.

Alternatively or in addition, the effluent gas entraining the active-metal carbide may be cooled by mixing with an endothermically decomposable gas. More particularly, an endothermically decomposable gas may be introduced into the flow of the effluent gas emerging from the furnace. Examples of suitable endothermically decomposable gasses include light hydrocarbons, such as methane, ethane, and propane, and mixtures thereof. At temperatures above 900° C., for example, $$CH_4 \rightarrow C + 2H_2 \quad (4)$$

occurs spontaneously and absorbs significant heat. At lower temperatures, however, the reaction is non-spontaneous. Accordingly, introduction of one or more hydrocarbons, such as methane, is expected to cool the effluent gas entraining the active-metal carbide to temperatures appropriate for subsequent reaction, as described below.

At 22 nitrogen is introduced into the cooled effluent gas entraining the carbide of the active metal, to yield a cyanamide of the active metal and elemental carbon. In examples in which calcium carbide is entrained in the cooled effluent gas, the cyanamide product is calcium cyanamide, $$CaC_2 + N_2 \rightarrow CaCN_2 + C. \quad (5)$$

Eq 5 represents the Franck-Caro process for conversion of calcium carbide to calcium cyanamide. Analogous reactivity is expected for active metals besides calcium, that form acetylide-type carbides under the conditions of eq 3. An acetylide-type carbide is a carbide having a relatively short C—C bond length, which reacts spontaneously with water to form acetylene. Analogous reactivity may also be observed for active metals that form non-acetylide-type carbides, such as magnesium.

In some examples, nitrogen may be introduced to the effluent gas entraining the active-metal carbide in a fluidized-bed reactor, where the nitrogen and the effluent gas are passed through the granular active-metal carbide at a velocity high enough to suspend the solid in a pseudofluid state. In some examples, introducing nitrogen to the cooled effluent gas includes maintaining a positive (e.g., high-velocity) flow of the effluent gas to prevent backflow of the nitrogen into the furnace. This can be achieved by discharging the fluidized-bed reactor into a chamber of pressure $P_3$ that is lower than $P_2$. This strategy not only discourages the backflow of nitrogen into the furnace (which could result in the formation of an active-metal cyanide) but also enables additional cooling of the active metal cyananamide intermediate via further expansion of the effluent gas. In some examples, the gas at $P_3$ may cool by expansion to less than 900° C.

At 24 the cyanamide of the active metal (M) is acidically hydrolyzed to yield a cyanamide compound and a salt of the active metal—e.g., $$M_n CN_2 + 2H^+ \rightarrow NH_2CN + nM^{(3-n)+}, \quad (6)$$

where $NH_2CN$ corresponds to the cyanamide monomer itself. In some examples, the cyanamide of the active metal may acidically hydrolyzed with water and carbon dioxide as the acid source. Under mildly basic conditions, cyanamide dimerizes into 2-cyanoguanidine, $$2NH_2CN \rightarrow (NH_2)_2(CN)_2, \quad (7)$$

which, if desired, is rearranged thermally to form the cyclic trimer melamine, $$(NH_2)_2(CN)_2 \rightarrow (NH_2)_3C_3N_3 \quad (8)$$

Accordingly, the cyanamide compound may include one or more of cyanamide monomer, 2-cyanoganadine, and melamine. Cyanamide compounds are useful as nitrogen-rich fertilizers and as precursors for chemical synthesis, including pharmaceutical syntheses. Cyanamide compounds may also be used as fuels and as 'ammonia carriers'—i.e., storable, transportable substances that are controllably decomposable to yield ammonia. Over a vanadium pentoxide/zinc catalyst, for example, $$(NH_2)_2(CN)_2 + 4H_2O \rightarrow 2CO_2 + 4NH_3. \quad (9)$$

In examples in which calcium cyananamide is acidically hydrolyzed with water and carbon dioxide as the acid source, the by-product of the hydrolysis includes one or more of calcium carbonate and calcium bicarbonate as salts of the active metal—e.g., $$CaCN_2 + H_2O + CO_2 \rightarrow NH_2CN + CaCO_3, \quad (10)$$

depending on the pH. The term 'salt' refers herein to an ensemble of oppositely charged ions, whether arranged in solid form or dissociated in fluid solution. In that context, the reader will understand that bicarbonate ($HCO_3^-$) salts of some elements (e.g., sodium) are stable as solids and in solution, whereas $HCO_3^-$ salts of other elements (e.g., calcium) may be stable only in solution. Accordingly, 'calcium bicarbonate' refers herein to a dissolved material comprising $Ca^{2+}$ and $HCO_3^-$ in a 1:2 ratio.

The transformation in eq 10 can be conducted in an aqueous slurry, from which the elemental carbon by-product of the cyanamide synthesis of eq 5 may be separated. At 26 of process 10, accordingly, the elemental carbon by-product cyanamide synthesis is optionally separated from a product of hydrolysis of the calcium cyanamide. In some examples, the separated elemental carbon may be used in the feedstock, as noted hereinabove. In other examples, the separated elemental carbon may be combusted to generate heat for one or more stages of process 10.

Despite the advantages of separating the elemental carbon by-product, the elemental carbon alternatively may be used without separation from the hydrolysis products. For instance, unseparated elemental carbon and calcium carbonate and/or calcium bicarbonate may be dried and subjected to combustion conditions. In this manner, the one or more of the calcium carbonate and the calcium bicarbonate may be heated by combustion of the elemental carbon.

At 28 the salt of the active metal, which is a product of the hydrolysis, is heated to yield a recovered oxide of the active metal. For instance the one or more of the calcium carbonate and the calcium bicarbonate may be heated to yield recovered calcium oxide—e.g., $$CaCO_3 \rightarrow CaO + CO_2, \text{ or} \quad (11)$$

$$Ca(HCO_3)_2 \rightarrow CaO + H_2O + 2CO_2. \quad (12)$$

In some examples, the heating may be used to dry these salts prior to thermolysis. In some examples, accordingly, the active metal oxide used in 12 above may include an active metal oxide, such as calcium oxide, recovered in this manner. Recovery of CaO by thermolysis, as in eqs 11 and 12, is less expensive and more environmentally sustainable than repeated thermolysis of natural limestone, which may release toxins such as mercury and/or arsenic. Furthermore, the carbon dioxide released in eqs 11 and 12 may also be recaptured. Accordingly, in examples in which the acid hydrolysis at 24 employs carbon dioxide, the carbon dioxide may include recaptured carbon dioxide released by heating the one or more of the calcium carbonate and the calcium bicarbonate.

In some examples, the heat used to recover the oxide of the active metal may include reclaimed heat. Eq 5, for instance, is known to be a significantly exothermic reaction. Thus, the heat used to recover the oxide of the active metal may include heat reclaimed from introducing nitrogen to the cooled effluent gas entraining the active-metal carbide, such as calcium carbide. In other examples, the reclaimed heat may derive from the cooling of the effluent gas.

In other examples, heat used to recover the oxide of the active metal may derive from external combustion. In example in which the elemental carbon by-product is separated at 26, the elemental carbon may be combusted externally as a heat source for recovery of the oxide of the active metal. In other examples, the CO effluent gas can be combusted to yield such heat.

No aspect of the above process should be interpreted in a limiting sense, because numerous variations, extensions, and omissions are also envisaged. For example, as the effluent gas that carries the active-metal carbide intermediate includes CO (from eq 3), process 10 may further comprise passing the effluent gas over a water-gas shift catalyst, to yield hydrogen, $$CO + H_2O \rightarrow CO_2 + H_2. \quad (13)$$

In variants in which an endothermically decomposable gas (e.g., methane) is used at 20 to effect cooling of the effluent gas, and wherein a portion of the endothermically decomposable gas is still present after formation of the active-metal cyanamide, that portion may be subject to cracking conditions prior to passing the effluent gas over the water-gas shift catalyst. In other words, high-temperature cracking enacted at 20, fluidically downstream of carbide formation, may be supplemented by additional low-temperature and/or catalytic cracking downstream of cyanamide formation, to yield additional hydrogen. Cracking may be supported by resistive heating of the effluent gas, for instance. In more particular examples, the fluidized carbon formed by such cracking may treated with high-temperature steam to yield carbon monoxide and hydrogen, $$C + H_2O \rightarrow CO + H_2. \quad (14)$$

fluidically upstream of the water-gas shift reaction.

The mode of utilization of the hydrogen prepared in eqs 13 and 14 is not particularly limited. In some examples, the hydrogen may be included in the stream of carrier gas supplied at 16 of method 10. Incorporation of hydrogen into the carrier gas may be more desirable than incorporation of methane itself, which may contain impurities that introduce undesirable process variables. In other examples, the hydrogen may be converted to heat or electrical energy for carbide formation at 16 or elsewhere in process 10.

Furthermore, reclaimed heat or heat derived from combustion of the elemental-carbon by-product or any combustible component of the effluent gas, such as hydrogen, may be used not only to recover the oxide of the active metal, but, alternatively or in addition, to re-melt the feedstock at 14 of process 10.

Figure 2:
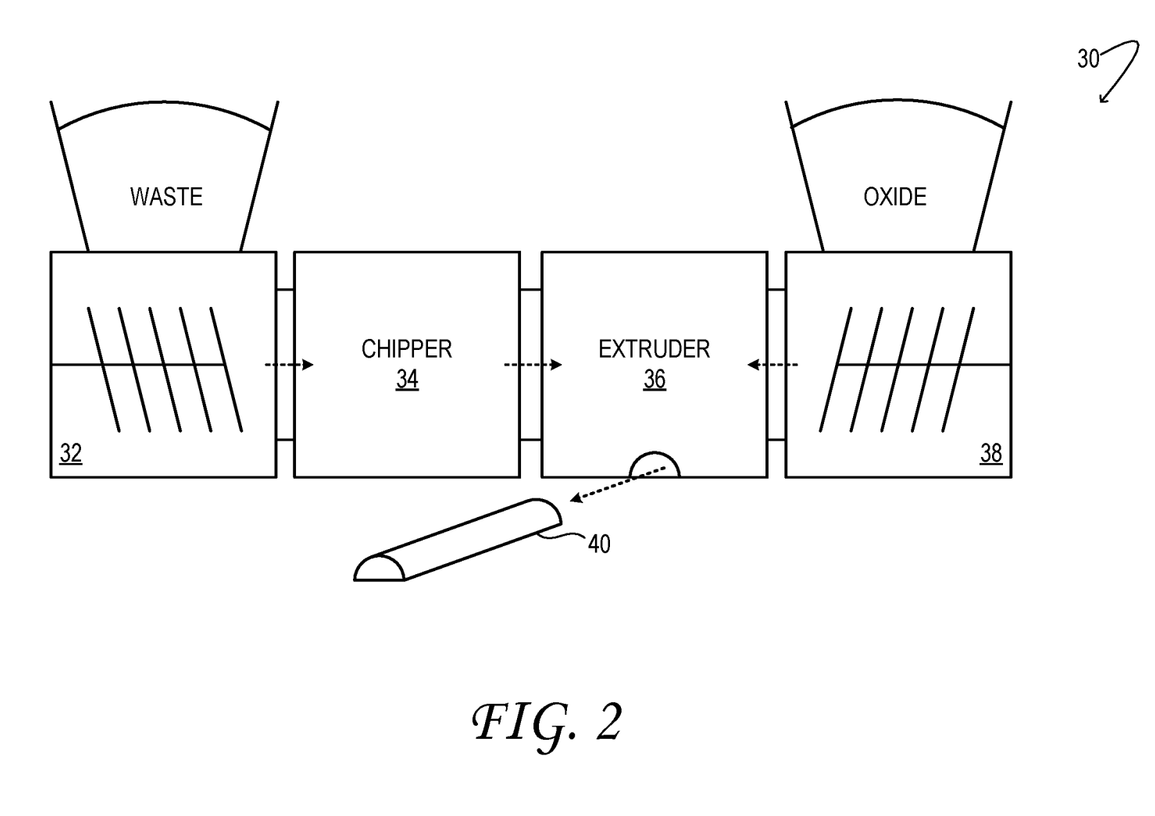
FIG. 2 shows aspects of an example feedstock-preparation system in connection to the process of FIG. 1.

FIG. 2 shows aspects of an example feedstock-preparation system 30 that may be used in connection to process 10. The feedstock-preparation system includes a hydrophobic-waste hopper 32 and a chipper 34. The hydrophobic-waste hopper is configured to receive hydrophobic waste and to convey the hydrophobic waste to the chipper. The chipper is configured to chip the hydrophobic waste into particles of a desired particle-size distribution.

Feedstock-preparation system 30 also includes an extruder 36 and an active-metal-oxide hopper 38. The extruder is configured to receive the chipped hydrophobic waste from chipper 34 and to receive active-metal oxide from the active-metal-oxide hopper. The extruder is configured to mechanically combine and intimately blend the chipped hydrophobic waste and the active metal oxide and to force the blended mixture through an orifice to form an extrusion 40 of active-metal oxide encapsulated in hydrophobic waste, which is suitable for use as a feedstock in process 10. In some examples, the extruder may be configured also to receive elemental carbon for incorporation into the feedstock.

Figure 3A:
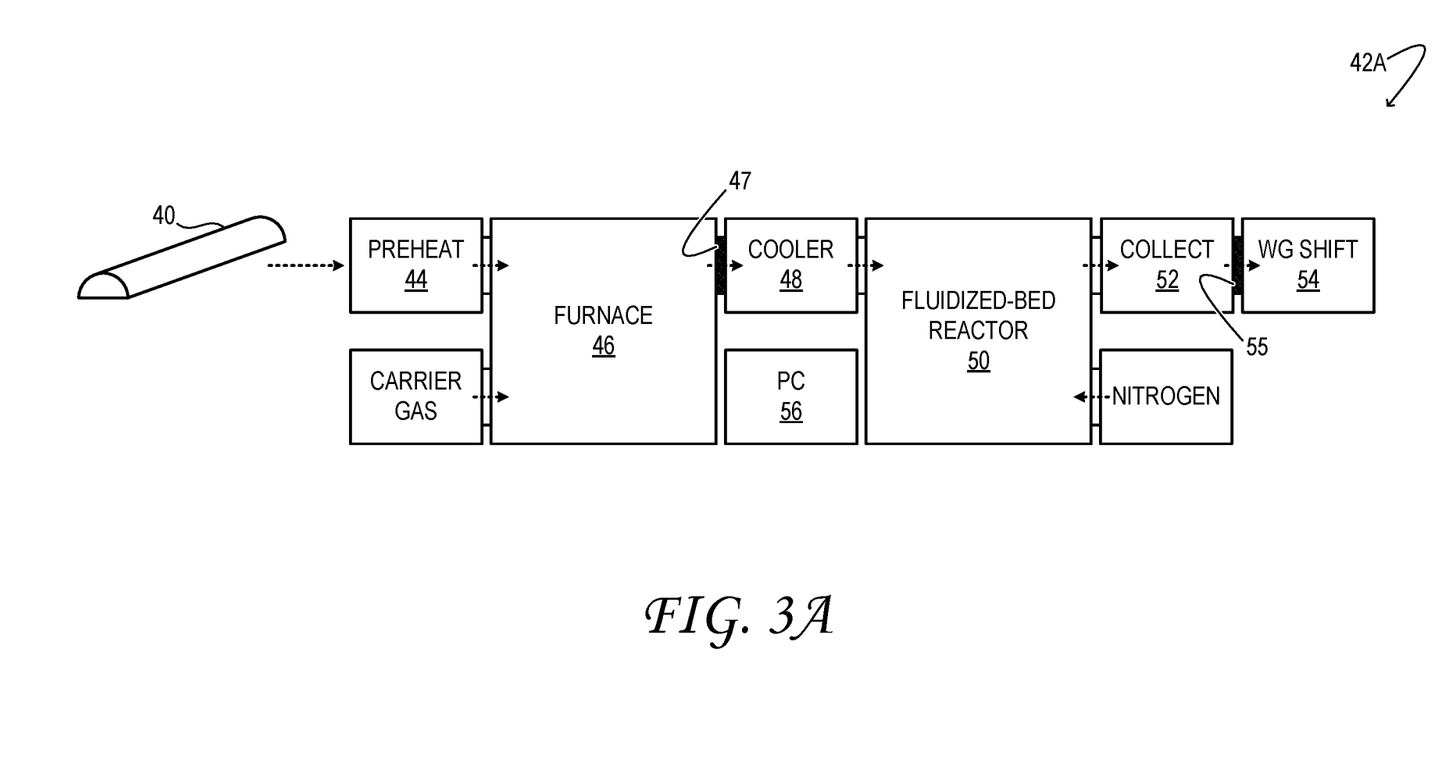
FIGS. 3A and 3B show aspects of example feedstock-reactor systems in connection to the process of FIG. 1.

FIG. 3A shows aspects of an example feedstock-reactor system 42A that may be used in connection to process 10. The feedstock-reactor system includes pre-heater 44 and a furnace 46. The pre-heater is configured to receive feedstock material and to pre-heat the feedstock material to a temperature suitable for entry into the furnace. The furnace is configured to receive pre-heated feedstock material from the pre-heater together with the carrier gas used in process 10. The furnace is configured to heat the pre-heated feedstock material and the carrier gas to a temperature at which eq 3 occurs with favorable kinetics. In some examples, the furnace may comprise an electric-arc furnace. In more particular examples, the furnace may comprise a rotating arc and/or hollow-electrode electric-arc furnace. In the illustrated example, a size-exclusion sieve 47 is arranged fluidically downstream of the furnace.

Feedstock-reactor system 42A also includes an optional cooler 48 and fluidized-bed reactor 50. Furnace 46 is configured to discharge the effluent gas entraining the active-metal carbide to cooler 48. In some examples, the effluent gas may be discharged through a sieve that achieves size selection of the entrained particles of the active-metal carbide. The cooler is configured to cool the effluent gas entraining the active-metal carbide and to discharge the cooled effluent gas entraining the active metal carbide to the fluidized-bed reactor. In some examples, the cooler is configured to introduce an endothermically decomposable gas into the effluent gas flow. The fluidized-bed reactor is configured to receive the cooled effluent gas entraining the active-metal carbide, to receive also nitrogen, and to facilitate reaction of the nitrogen and the active-metal carbide to form fluidized active-metal cyanamide particles.

Feedstock-reactor system 42A also includes a collection chamber 52 and, optionally, a water-gas shift reactor 54. Fluidized-bed reactor 50 is configured to discharge the effluent gas entraining the active-metal cyanamide to the collection chamber. In the illustrated example, the collection chamber includes a filter 55 or other separation component configured to pass the effluent gas on to the water-gas shift reactor but to retain the active-metal cyanamide. The water-gas shift reactor is configured to convert the CO component of the effluent gas to $H_2$ (eq 13). In some examples, optional cracking and/or producer-gas forming stages are arranged within or fluidically upstream of the water-gas shift reactor.

Feedstock-reactor system 42A also includes a process controller 56. The process controller is configured to receive sensory input from a plurality of sensors arranged in the feedstock-reactor system. Such sensors may include temperature sensors, pressure sensors, flow sensors, fill sensors, and the like. The sensors may be arranged on preheater 44, furnace 46, cooler 48, fluidized-bed reactor 50, collection chamber 52 and/or water-gas shift reactor 54, for example. The process controller is configured to provide control output to a plurality of actuators arranged in the feedstock-reactor system. Such actuators may include flow actuators that control the flow of carrier gas and/or nitrogen, or the flow between fluidically connected components of the feedstock-reactor system. Other actuators may include heating actuators for pre-heater 44, furnace 46, fluidized-bed reactor 50, and/or water-gas shift reactor 54, and cooling actuators for cooler 48, for example. Process controller 56 includes a computer system configured to execute a process for controlling any, some, or all of the control outputs based on any, some, or all of the sensory inputs, and further based on desirable process setpoints and/or input from a human operator. In some examples, the process controller may be configured to control any, some, or all of the control outputs in a closed-loop manner, based on any, some, or all of the sensory inputs and/or process setpoints.

Figure 3B:
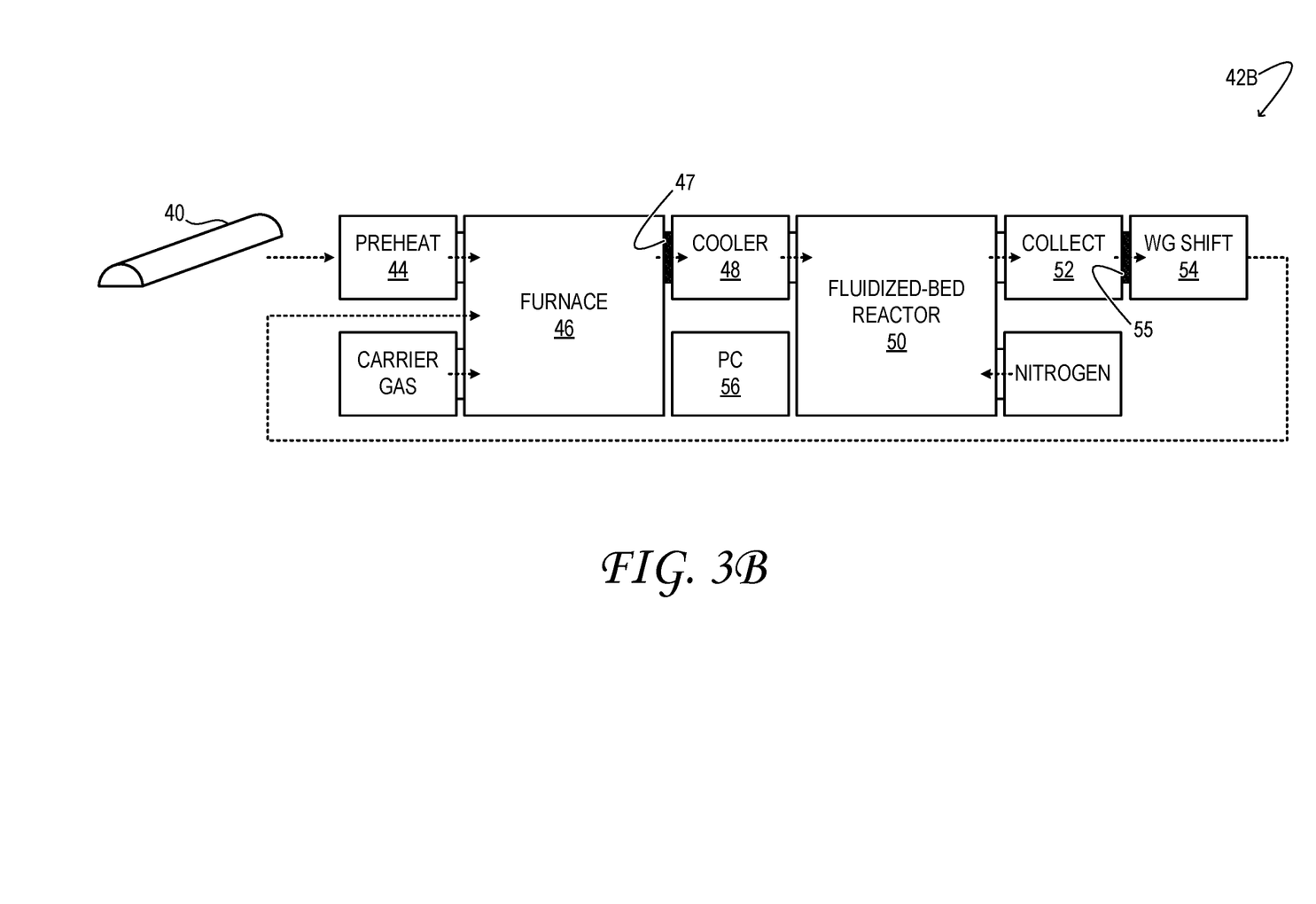

FIG. 3B shows aspects of another example feedstock-reactor system 42B that may be used in connection to process 10. In feedstock-reactor system 42B, a portion of the discharge from water-gas shift reactor 54 is fed back to furnace 46 to supplement the carrier gas admitted to the furnace. That portion may include hydrogen formed in the water-gas shift reactor and/or any non-reactive gas transmitted through the water-gas shift reactor.

Figure 4:
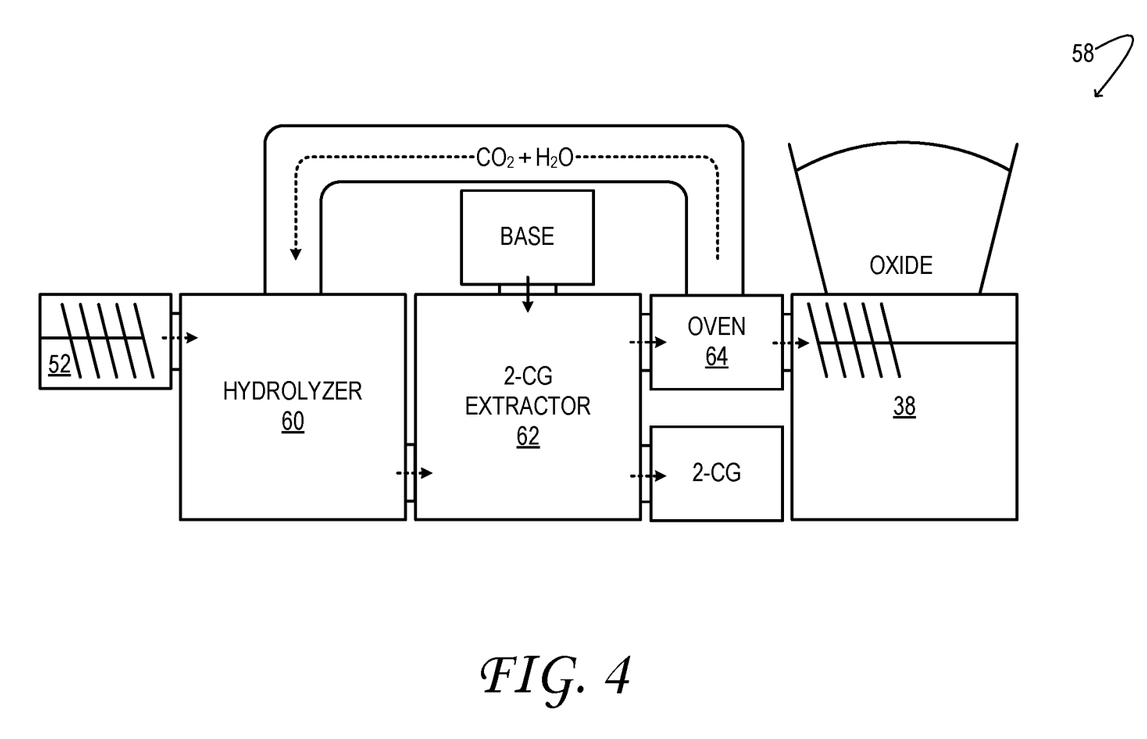
FIG. 4 shows aspects of an example cyanamide-reactor system in connection to the process of FIG. 1.

FIG. 4 shows aspects of an example cyanamide-reactor system 58 that may be used in connection to process 10. The cyanamide-reactor system includes hydrolyzer 60 and 2-cyanoguanadine (2-CG) extractor 62. The hydrolyzer is configured to receive the active-metal cyanamide from collection chamber 52 and to receive also an equimolar mixture of water and $CO_2$. The hydrolyzer is configured to facilitate acidic hydrolysis of the active-metal cyanamide and to release the hydrolysate to the 2-CG extractor. To that end, the 2-CG extractor is configured to receive a base (as understood in the context of acid-base chemistry) and to combine the hydrolysate and the base, causing the cyanamide component of the hydrolysate to dimerize into 2-CG.

Cyanamide-reactor system 58 also includes oven 64. From 2-CG extractor 62, a carbonate and/or bicarbonate component of the hydrolysate is conveyed to the oven, which is configured to heat the carbonate and/or bicarbonate component to a temperature at which the thermolysis of eqs 11 and 12 is spontaneous. Gaseous products of the thermolysis, water vapor and $CO_2$ are conveyed back to hydrolyzer 60, while the active-metal oxide component is conveyed to active-metal-oxide hopper 38.

No aspect of the process componentry of FIGS. 2 through 4 should be understood in a limiting sense, because other forms of componentry may be used, alternatively or in addition, in connection to the processes, functions, and acts disclosed herein.

It will be understood that the configurations and/or approaches described herein are exemplary in nature, and that these specific examples are not to be considered in a limiting sense, because numerous variations are possible. The specific routines or methods described herein may represent one or more of any number of processing strategies. As such, various acts illustrated and/or described may be conducted in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The following additional documents are also hereby incorporated herein by reference for all purposes:

R. K. Graupner and J. D. Hultine, PRODUCTION AND USE OF CYANOGUANIDINE AND CYANAMIDE, International Patent Application Publication Number WO 2012/123378 A1, 20 Sep. 2012.

R. K. Graupner and J. D. Hultine, PRODUCTION AND USE OF CYANOGUANIDINE AND CYANAMIDE, International Patent Application Publication Number WO 2012/123380 A2, 20 Sep. 2012.

The invention claimed is:

1. A process to extract carbon from hydrophobic waste, the process comprising:
   blending the hydrophobic waste with an oxide of an active metal to form a storable, moisture-resistant feedstock for subsequent carbide synthesis, the feedstock comprising the hydrophobic waste and the oxide of the active metal in a predetermined ratio;

heating the feedstock in a furnace to yield an effluent gas entraining a carbide of the active metal;

cooling the effluent gas entraining the carbide of the active metal;

introducing nitrogen into the cooled effluent gas entraining the carbide of the active metal, to yield a cyanamide of the active metal and elemental carbon; and acidically hydrolyzing the cyanamide of the active metal to yield a cyanamide compound and a salt of the active metal.

2. The process of claim 1 wherein the oxide of the active metal includes calcium oxide.

3. The process of claim 2 wherein acidically hydrolyzing includes hydrolyzing with water and carbon dioxide, and wherein the salt of the active metal includes one or more of calcium carbonate and calcium bicarbonate.

4. The process of claim 1 wherein the cyanamide compound includes one or more of 2-cyanoguanidine and melamine.

5. The process of claim 1 wherein the hydrophobic waste includes one or more of waste plastic and roof shingle.

6. The process of claim 1 wherein blending the hydrophobic waste with the oxide of the active metal includes extruding the hydrophobic waste with the oxide of the active metal.

7. The process of claim 1 wherein cooling the effluent gas includes cooling via expansion.

8. The process of claim 1 wherein cooling the effluent gas includes cooling by introduction of an endothermically decomposable gas.

9. The process of claim 1 further comprising conveying the feedstock into the furnace, wherein said conveying includes re-melting the feedstock with excess heat released in the process.

10. The process of claim 1 wherein introducing nitrogen to the cooled effluent gas includes maintaining a positive flow of the effluent gas to prevent backflow of the nitrogen into the furnace.

11. A process to extract carbon from hydrophobic waste, the process comprising:

blending the hydrophobic waste with calcium oxide to form a storable, moisture-resistant feedstock for subsequent carbide synthesis, the feedstock comprising the hydrophobic waste and the calcium oxide in a predetermined ratio;

heating the feedstock in a furnace to yield an effluent gas entraining calcium carbide;

cooling the effluent gas entraining the calcium carbide;

introducing nitrogen into the cooled effluent gas entraining the calcium carbide to yield calcium cyanamide and elemental carbon; and hydrolyzing the calcium cyanamide with water and carbon dioxide to yield a cyanamide compound and one or more of calcium carbonate and calcium bicarbonate.

12. The process of claim 11 wherein the calcium oxide includes recovered calcium oxide, the process further comprising heating the one or more of the calcium carbonate and the calcium bicarbonate to yield the recovered calcium oxide.

13. The process of claim 12 wherein the one or more of the calcium carbonate and the calcium bicarbonate is heated with heat reclaimed from introducing nitrogen to the cooled effluent gas entraining the calcium carbide.

14. The process of claim 12 further comprising separating the elemental carbon from the calcium cyanamide or from a product of hydrolysis of the calcium cyanamide.

15. The process of claim 14 wherein heating the feedstock includes heating by combustion of the separated elemental carbon.

16. The process of claim 12 wherein the one or more of the calcium carbonate and the calcium bicarbonate is combined with the elemental carbon, and wherein the one or more of the calcium carbonate and the calcium bicarbonate is heated by combustion of the elemental carbon.

17. The process of claim 12 wherein the carbon dioxide includes carbon dioxide released by heating the one or more of the calcium carbonate and the calcium bicarbonate.

18. The process of claim 11 wherein the effluent gas includes carbon monoxide, the process further comprising passing the effluent gas over a water-gas shift catalyst to yield hydrogen.

19. The process of claim 11 wherein heating the feedstock includes heating under a flow of carrier gas, and wherein the effluent gas includes the carrier gas.

20. The process of claim 19 wherein the carrier gas includes one or more of helium, argon, hydrogen and carbon dioxide.

* * * * *